(12) United States Patent
Proksa et al.

(10) Patent No.: US 6,285,733 B1
(45) Date of Patent: Sep. 4, 2001

(54) COMPUTED TOMOGRAPHY METHOD UTILIZING A CONICAL RADIATION BEAM

(75) Inventors: Roland Proksa; Michael Grass, both of Hamburg (DE)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/408,793

(22) Filed: Sep. 30, 1999

(30) Foreign Application Priority Data

Oct. 1, 1998 (DE) .............................................. 198 45 133

(51) Int. Cl.$^7$ ........................................................ A61B 6/03
(52) U.S. Cl. .................................. 378/15; 378/4; 378/901
(58) Field of Search ................................. 378/4, 15, 901

(56) References Cited

U.S. PATENT DOCUMENTS

| | | | | |
|---|---|---|---|---|
| 5,170,439 | * | 12/1992 | Zeng et al. ........................... | 382/131 |
| 5,778,038 | * | 7/1998 | Brandt et al. ........................ | 378/4 |
| 5,999,587 | * | 12/1999 | Ning et al. .......................... | 378/4 |
| 6,075,836 | * | 6/2000 | Ning .................................... | 378/98.12 |

OTHER PUBLICATIONS

"Practical cone–beam algorithm", by L.A. Feldkamp, Journal of Optical Soc. Am. A/vol. 1, No. 6, 1984, pp. 612–619.

\* cited by examiner

*Primary Examiner*—David V. Bruce
(74) *Attorney, Agent, or Firm*—John F. Vodopia

(57) ABSTRACT

The invention relates to a computed tomography method in which the examination zone is scanned along a circular path by means of a conical radiation beam. The computation required for the reconstruction of the absorption distribution in the examination zone can be reduced by taking the following steps: a) rebinning of the measuring data so as to form a number of groups, each group containing a plurality of planes which extend parallel to one another and parallel to the axis of rotation, each plane containing a respective fan beam, b) one-dimensional filtering of the data, produced by the rebinning, of each group in the direction perpendicular to the direction of the planes, and c) reconstructing the spatial distribution of the absorption from the filtered data of different groups.

6 Claims, 5 Drawing Sheets

COMPUTED TOMOGRAPHY METHOD UTILIZING A CONICAL RADIATION BEAM

BACKGROUND OF THE INVENTION

1. Field of the Invention

The invention relates to a computed tomography method which includes the following steps: generating, while using a radiation source, a conical radiation beam which traverses an examination zone or an object present therein, generating a circular relative motion, including a rotation about an axis of rotation, between the radiation source on the one side and the examination zone or the object on the other side, acquiring, while using a detector unit, measuring data which is dependent on the intensity in the radiation beam to the other side of the examination zone during the relative motion, reconstructing the spatial distribution of the absorption within the examination zone from the acquired measuring data. The invention also relates to a computed tomography apparatus for carrying out the above method.

2. Description of Related Art

A method of the kind set forth is known from a publication by L. A. Feldkamp et al. "Practical cone-beam algorithm", Journal of Optical Soc. Am. A/Vol. 1, No. 6, 1984, pp. 612–619. The known method in principle consists of the following steps:

a) multiplying, for all radiation source positions, all measuring values by a weighting factor which corresponds to the cosine of the angle enclosed by the ray along which the measuring value has been acquired with respect to the central ray;

b) subjecting the measured values thus weighted to a high-pass filtering operation.

c) backprojecting the measured values into the examination zone along the rays along which they have been measured. The contribution of a measuring value to the absorption value of a voxel must then be weighted by a factor which is dependent on the distance between the relevant voxel and the radiation source position.

Because this last step must be carried out for all voxels of the volume to be reconstructed and for all radiation source positions, it requires a long calculation time. It is a further drawback of the known method that it only enables the reconstruction of the absorption in voxels which have been continuously exposed to X-rays during the examination. Such voxels are situated in a discus-shaped region which is concentrically situated relative to the axis of rotation. However, it is desirable to perform a reconstruction in a flat, cylindrical slab-like region. If the reconstruction, however, is limited to the slab-like region in the conical beam which is exposed to X-rays in all radiation source positions, only a very narrow reconstruction region will be obtained.

Citation of a reference herein, or throughout this specification, is not to construed as an admission that such reference is prior art to the Applicant's invention of the invention subsequently claimed.

SUMMARY OF THE INVENTION

It is an object of the present invention to propose a computed tomography method of the kind set forth in which the amount of calculation work is reduced and reconstruction of the absorption distribution is possible in a thicker, flat slice of the examination zone. On the basis of a method of the kind set forth this object is achieved according to the invention by taking the following steps:

a) rebinning the measuring data so as to form a number of groups, each group containing a plurality of planes which extend parallel to one another and parallel to the axis of rotation and in each of which a respective fan beam is situated, b) one-dimensional filtering of the data produced by the rebinning in each group in a direction perpendicular to the direction of the planes, c) reconstructing the spatial distribution of the absorption by backprojection of the filtered data of a plurality of groups.

Whereas according to the known method the measuring values acquired in the individual radiation source positions are always directly subjected to a filtering operation, in the method according to the invention there is first performed a rebinning operation during which fan beams picked up in different radiation source positions are group-wise combined, after which filtering takes place. The advantage of the additional rebinning operation resides in the fact that the contributions of the individual measured values to a voxel need not be multiplied by a distance-dependent factor during the subsequent reconstruction of the absorption distribution. The reconstruction is thus significantly simplified. The image quality is also enhanced. Moreover, an attractive ratio of the irradiated volume to the volume in which the absorption distribution can be reconstructed is obtained.

The invention is also based on the recognition of the fact that the absorption can be reconstructed in each voxel if the voxel has been irradiated from an angular range of at least 180°. It can be demonstrated that all voxels which satisfy this requirement are situated in a flat slab which extends perpendicularly to the axis of rotation and whose thickness is greater than the dimensions at the edges of the discus-shaped region in which the absorption can be reconstructed by means of the known method.

The rebinning on a flat, rectangular virtual detector, which extends perpendicularly to the planes of each group and contains the axis of rotation, significantly simplifies the subsequent one-dimensional filtering operation.

The slab in which the absorption distribution can be reconstructed contains voxels which have been irradiated from an angular range of more than 180°. However, because the reconstruction requires only an irradiation angle range of 180° (being the angular range covered by the (parallel) projection of the rays from the radiation source to a voxel onto a plane perpendicular to the axis of rotation, or covered by the components of the vectors from the radiation source to the voxel in the plane of rotation of the radiation source) measuring values from some radiation source positions may be ignored. A simple possibility of determining the radiation source positions whose measuring data are to be taken into account for the reconstruction of the absorption in individual voxels includes reconstructing the absorption of voxels with an irradiation angle range of at least 180° while taking into account the filtered measuring data from exclusively the radiation source positions which are separated from the voxel by a plane which contains the axis of rotation and extends perpendicularly to the plane defined by the relevant voxel and the axis of rotation.

The absorption distribution in said slab can in principle be reconstructed by taking into account only as many radiation source positions for the reconstruction of all voxels as are required to obtain an irradiation angle range of exactly 180° is obtained. However, this slab also contains voxels with an irradiation angle range of 360°. If such voxels were also reconstructed with an irradiation angle range of only 180°, the signal-to-noise ratio obtained for these voxels would not be as good as possible. Therefore, in a hybrid reconstruction method, the volume of the slab that can be reconstructed is subdivided into two sub-volumes: a first sub-volume which contains exclusively voxels which have been irradiated from all radiation source positions (i.e., with an irradiation angle range of 360°), and a second sub-volume in which the irradiation angle range is less than 360° (i.e., with an irradiation angle range of at least 180° but less than 360°). During the reconstruction of the absorption in the voxels of the first sub-volume, all measuring values are taken into account whereas only the measuring values from an irradiation angle range of 180° are taken into account for the reconstruction of the voxels in the second sub-volume.

A computed tomography apparatus for carrying out the method according to the invention includes a radiation source, a detector unit which is coupled thereto, a drive device for making an object present in the examination zone and the detector device perform a rotation about the axis of rotation relative to one another, and a reconstruction unit for reconstructing the spatial distribution of the absorption within the examination zone from the measuring data acquired by the detector unit, wherein the reconstruction unit further includes means for the rebinning of the measuring data so as to form a plurality of groups, each group containing several planes which are parallel to the axis of rotation and each of which contains a fan beam, means for the one-dimensional filtering of the data, produced by the rebinning, of each group in the direction perpendicular to the direction of the planes, and means for the reconstruction of the spatial distribution of the absorption from the filtered data of different groups.

In version of the method according to the invention, a part of the measuring values is not used for the reconstruction. These measuring values are associated with rays which are not required when the absorption distribution is to be reconstructed in a flat slab only. These rays have a small angle of aperture in a plane perpendicular to the axis of rotation and a comparatively large angle of aperture in a plane containing the axis of rotation. When the conical radiation beam is shaped, using a construction of the collimator device having edges which are mutually offset in the direction of the axis of rotation and which are shaped in such a manner that the conical radiation beam has an aperture at its center which is smaller than that at its edges, in such a manner that these rays do not even occur, the radiation load for a patient present in the examination zone will be reduced. This advantage is also obtained when the absorption distribution is reconstructed in a different manner, for example by means of an ART method.

BRIEF DESCRIPTION OF THE DRAWING

The invention will be described in detail hereinafter with reference to the drawings. Therein.

DETAILED DESCRIPTION OF THE PREFERRED EMBODIMENT

Figure 1:
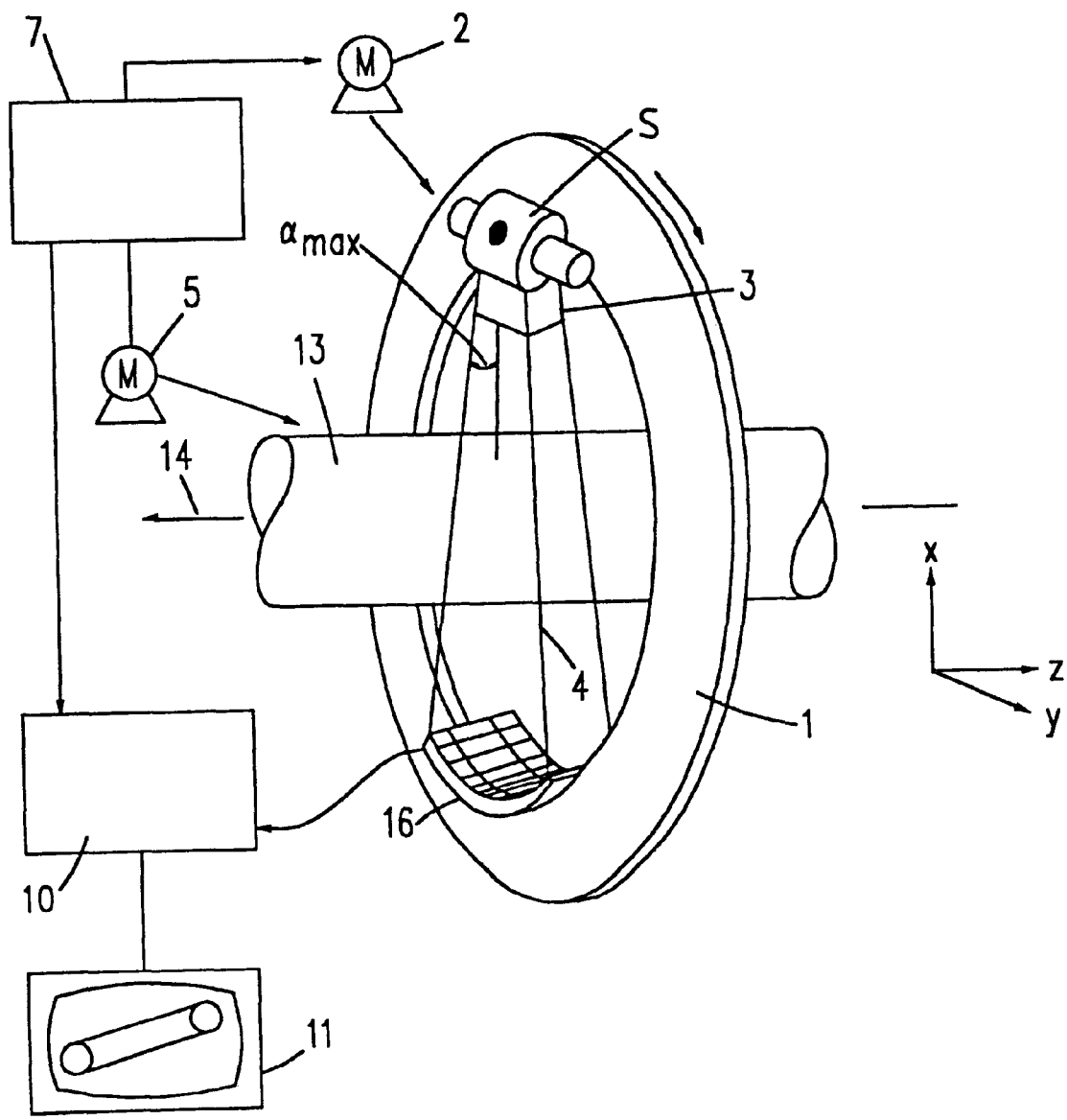
FIG. 1 shows a computed tomography apparatus in which the invention can be carried out.

The computed tomography apparatus shown in FIG. 1 includes a gantry 1 which is capable of rotation about an axis of rotation 14 which extends parallel to the z direction of the co-ordinate system shown in FIG. 1. To this end, a motor 2 drives the gantry at a preferably constant but adjustable angular speed. A radiation source S, for example an X-ray source, is connected to the gantry. The source is provided with a collimator device 3 which forms a conical radiation beam 4 from the radiation produced by the radiation source S, i.e. a radiation beam which has a finite dimension other than zero in the z direction as well as in a direction perpendicular thereto (i.e. in a plane perpendicular to the axis of rotation).

The radiation beam 4 traverses an examination zone 13 in which a patient may be accommodated on a patient table (both not being shown). The examination zone 13 is shaped as a cylinder which will be referred to hereinafter as the object cylinder 13. After having traversed the object cylinder 13, the X-ray beam 4 is incident on a two-dimensional detector unit 16 which is connected to the gantry 1 and comprises a number of detector rows, each of which comprises a plurality of detector elements. The detector rows are situated in planes perpendicular to the axis of rotation and on an arc of circle about the radiation source S; however, they may alternatively describe an arc of circle about the axis of rotation or be arranged along a straight line. Each detector element provides a measuring value for a ray of the radiation beam 4 in each position of the radiation source.

The angle of aperture of the radiation beam 4, denoted by the reference $\alpha_{max}$ (the angle of aperture is defined as the angle enclosed by a ray, situated at the edge of the radiation beam 4 in a plane perpendicular to the axis of rotation, relative to the plane of the central ray defined by the radiation source S and the axis of rotation 14), then determines the diameter of the object cylinder 13 within which the object to be examined is situated during the acquisition of the measuring values. The examination zone 13, or the object or the patient table, can be displaced parallel to the axis of rotation 14 or to the z axis by means of a motor 5. The speed of such transport in the z direction is preferably constant and adjustable. When the motors 5 and 2 are simultaneously activated, the radiation source S and the detector unit perform a helical scanning motion. However, when the motor 5 for the transport in the z direction is stationary and the motor 2 rotates the gantry separately, the radiation source S and the detector unit perform a circular scanning motion relative to the examination zone 13. Only this circular scanning motion will be considered hereinafter.

The measuring data acquired by the detector unit is applied to an image processing computer 10 which reconstructs therefrom the absorption distribution in a part of the examination zone 13 and, for example, displays it on a monitor 11. The two motors 2 and 5, the image processing computer 10, the radiation source S and the transfer of the measuring data from the detector unit 16 to the image processing computer 10 are controlled by a suitable control unit.

Figure 2:
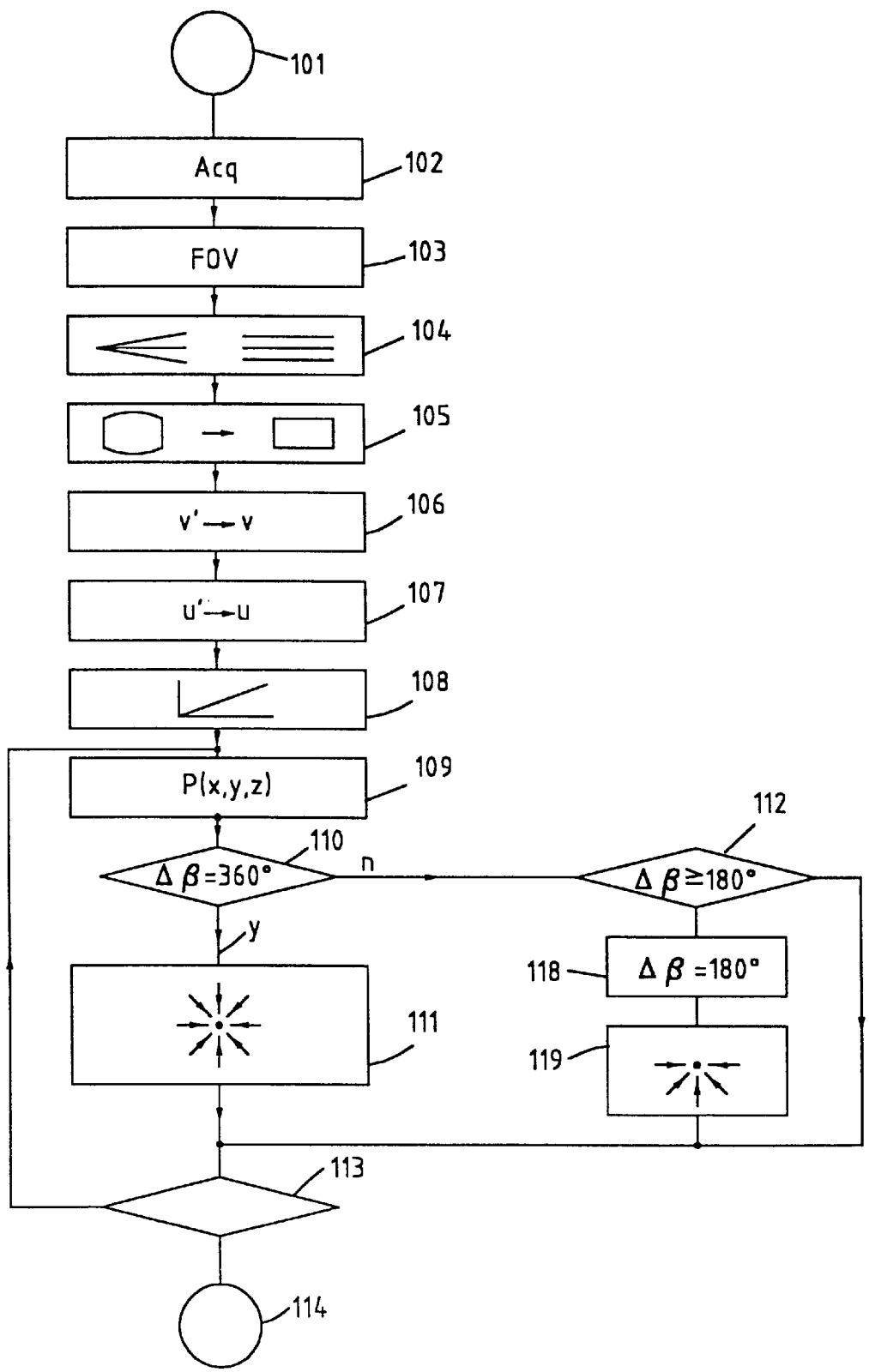
FIG. 2 shows a flow chart of the reconstruction method according to the invention.

FIG. 2 illustrates the execution of a measuring and reconstruction method which can be carried out by means of the computed tomography apparatus shown in FIG. 1.

After the initialization in the block 101, the gantry rotates at a constant angular speed. In the step 102 the radiation of the radiation source S is switched on and the measuring values then acquired by the detector elements of the detector unit 16 are stored in a memory of the image processing computer 10.

Figure 3:
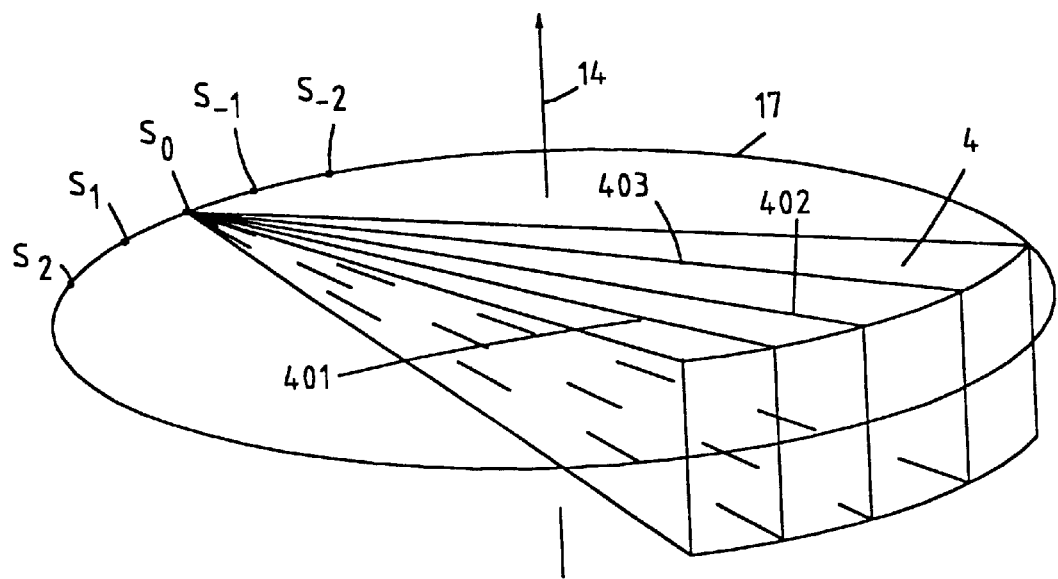
FIG. 3 shows a conical radiation beam generated in a radiation source position.

FIG. 3 shows the circular path 17 described around the axis of rotation 14 by the radiation source S and the detector unit 16. The radiation beam 4 is shown for a given radiation source position So. This conical radiation beam 4 can be composed from a plurality of flat fan beams which are situated in planes parallel to the axis of rotation, like the fan beams 401 . . . 403. Even though the rays of the conical radiation beam 4 can also be grouped in a different manner, the term "fan beam" hereinafter will be used only for rays which are situated in a common plane which is parallel to the axis of rotation 14. Such fan beams emanate from one radiation source position and are detected by a respective column of detector elements of the detector unit 16, which column is directed parallel to the direction of rotation. FIG. 3 shows that the emitted conical radiation beam is also measured in other positions of the radiation source (for example, $S_{-1}$, $S_1$ or $S_2$).

In the step 103 the diameter of the field of view (FOV) to be reproduced is defined. The diameter may correspond to the diameter of the examination zone 13 as defined by $\alpha_{max}$; however, it may also be smaller.

A rebinning operation is performed in the steps 104–107. The data is then resorted and re-interpolated as if it bad been measured with a different radiation source (a circular radiation source emitting parallel fan beams) and a different detector (a flat, rectangular "virtual" detector containing the axis of rotation).

In the step 104 first the fan beams from different radiation source positions are then combined so as to form a respective group, said beams being situated in mutually parallel planes. The fan beams associated with a respective group, therefore, satisfy the condition specifying that the sum of the angles $\alpha$ and $\beta$ must have the same value for all fan beams of this group. $\alpha$ is the angle enclosed by the plane of the fan beam relative to the plane of the central ray defined by the radiation source position and the axis of rotation, and is given by the position of the column of detector elements which have measured the relevant fan beam. $\beta$ is an angle which characterizes the radiation source position (for example, $S_0$) on the circle 17. When the fan beams for a radiation source position do not exactly satisfy this condition, an appropriate fan beam must be determined for this radiation source position by interpolation of the rays of neighboring fan beams.

Figure 4:
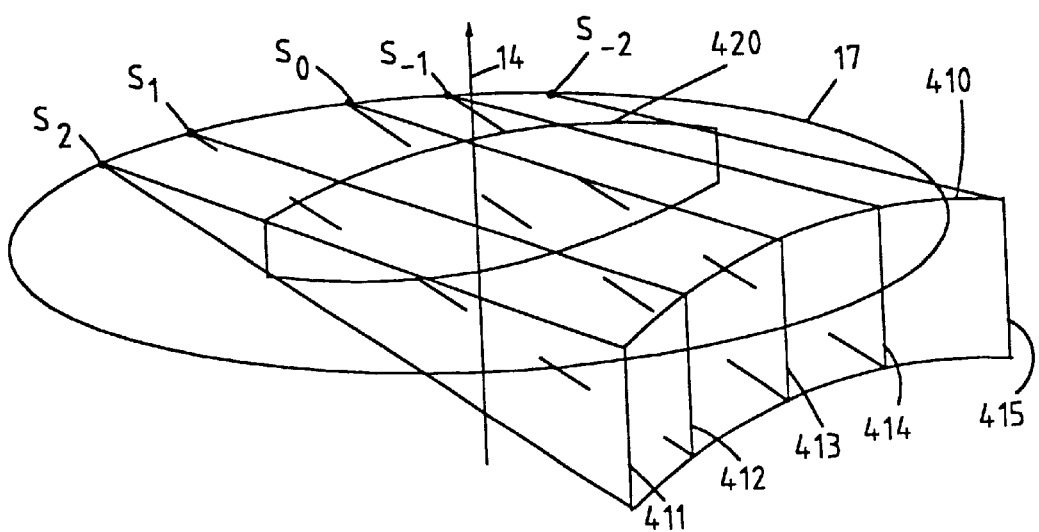
FIG. 4 shows the fan beams formed by rebinning in parallel planes.

FIG. 4 shows a group of fan beams thus formed. Each time one fan beam of each of the neighboring radiation source positions $S_{-2}$ . . . $S_0$ . . . $S_2$ belongs to a group. Each group can be characterized by the angle $\beta$ of the radiation source position (for example, $S_0$) whose fan beam which belongs to the group traverses the axis of rotation 14. (Generally speaking, this will be the central radiation source position, so the radiation source position $S_0$ in the example shown in FIG. 4). In that case there may be as many groups of fan beams as there are radiation source positions, but more groups or fewer groups are also feasible.

Figure 5:
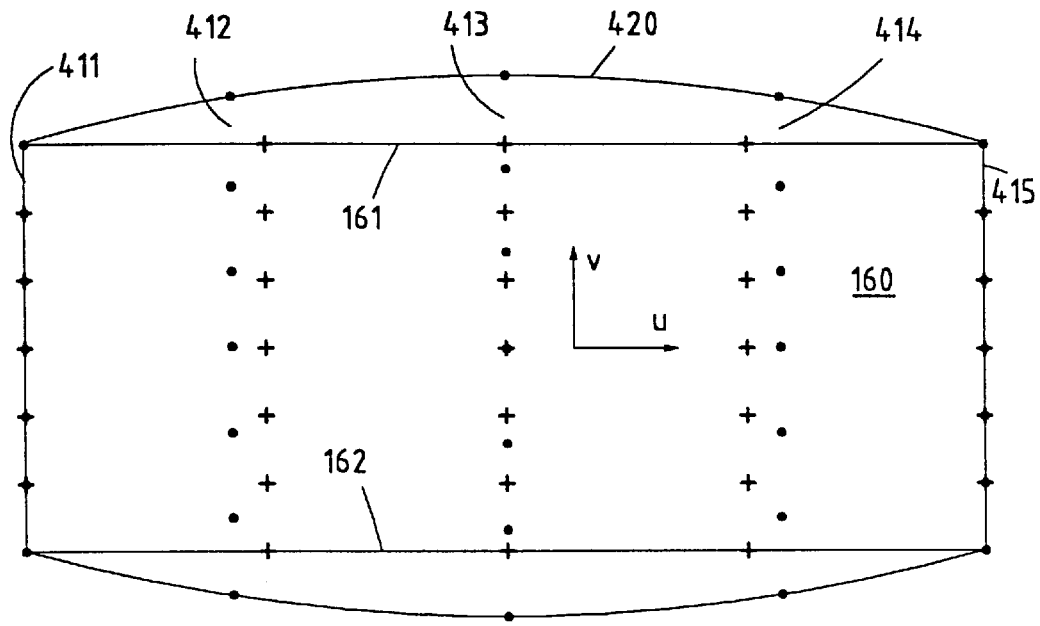
FIG. 5 is a cross-sectional view of these fan beams.

The fan beams thus determined, including the fan beams 411 . . . 415 shown in FIG. 4, define a radiation beam 410 which has a tent-like shape and is composed of fan beams which are situated in planes extending parallel to one another and parallel to the axis of rotation. FIG. 4 also shows the area of intersection 420 which is obtained when the radiation beam 410 is intersected by a plane which contains the axis of rotation 14 and extends perpendicularly to the planes of the fan beams 411 . . . 415. As is shown notably in FIG. 5, illustrating this area of intersection, the upper and lower edges are curved. This curvature is due to the fact that the radiation source positions at the center (for example, $S_0$) are situated further from the plane of intersection than those at the edges $S_2$ or $S_{-2}$ and that the fan beams all have the same angle of aperture, because the detector rows describe an arc of circle around the radiation source S. In the case of a different geometry of the detector rows, the shape of the plane of intersection 420 would be different. In the case of a flat detector unit (for example, a unit comprising straight detector rows), the curvature would be even more pronounced, because the fan beams situated at the edge, for example the beams 411 and 415, would then have a smaller angle of aperture.

Therefore, for each group of fan beams a rectangular virtual detector is defined in the flat area of intersection 420 (step 105), the upper edge 161 and the lower edge 162 of said virtual detector being defined by the dimensions of the outer fan beams 411 and 415, respectively, in the flat area of intersection. When the diameter of the field of view (FOV) to be reconstructed has been chosen so as to be smaller than the diameter of the examination zone 13, each time the outer fan beams (for example, 411, 415) of each group can be dispensed with. In that case the distance between the upper and lower edges 161 and 162 may be chosen so as to be larger than in the example shown in FIG. 5.

FIG. 5 also shows, symbolized by round dots, the puncture points of some rays, contained in the fan beams 411 . . . 415, through this virtual detector. Finally, crosses denote the supporting points of a regular Cartesian grid. The puncture points and the supporting points generally do not coincide. It appears on the one hand that the fan beams are situated nearer to one another at the outside than at the inside and that the puncture points of a fan beam are situated further from one another at the inside than at the outside. Therefore, in the two subsequent steps 106 and 107 the measuring points at the equidistant supporting points within the virtual detector 160 must be determined from the measuring values for the puncture points.

In the step 106 first a vertical interpolation is performed in such a manner that for all fan beams the supporting points in the vertical direction are situated at the same distance from one another as the puncture points or supporting points at the edge of the virtual detector 160. In the step 107 an interpolation is performed in the horizontal direction, so that interpolated values are obtained for supporting points which are situated at the same distance from one another in the horizontal direction within the virtual detector 160. The interpolation steps 105 and 106 may also be interchanged and possibly even combined.

The result of this interpolation in the horizontal and in the vertical direction is that the intensity of the radiation at the equidistant supporting points is obtained in a regular Cartesian grid in the virtual detector 160. The supporting points themselves define new fan beams again, which beams are situated in parallel planes at each time the same distance from one another. Only these new fan beams (which may be partly identical to the original fan beams) are used for the further reconstruction.

A part of the rays whose puncture points as situated outside the virtual window is not used in the steps 106 and 107. Therefore, it is advantageous to design the collimator 3 in such a manner that it does not contain the conical radiation beam. As a result, the radiation dose for the patient would be reduced. Instead of having straight edges extending perpendicularly to the axis of rotation, to this end the collimator device should have edges which are curved inwards, so that the fan beams which intersect the axis of rotation, or are situated at a small distance therefrom, have an angle of aperture which is smaller than that of fan beams which are situated at the outer edge of the radiation beam.

After the steps 103 to 107, the radiation intensity at the regular supporting points of the virtual detector 160 associated with the relevant group has thus been determined for each group of fan beams. This facilitates the necessary high-pass filter significantly, because only one-dimensional filtering of the data produced by the rebinning on the virtual detector 160 will then be required. Therefore, in the step 108 a one-dimensional filtering operation is performed on this data while utilizing a transfer factor which increases ramp-like as a function of the frequency. To this end, each time only the values of supporting points which succeed one another in the horizontal direction are taken into account. This filtering operation is performed for all groups of (new) fan beams.

The data determined after the rebinning and the filtering for the rays defined by the supporting points in the virtual window 160 is subsequently used for the reconstruction of the absorption distribution in the examination zone by way of backprojection. As opposed to the known method mentioned at the beginning, because of the preceding steps 103 to 108 it is not necessary to weight the contributions of individual rays to the absorption value of a voxel by a factor which is dependent on the distance between the relevant voxel and the radiation source position.

For the backprojection it would in principle suffice to take into account, for each voxel, data from groups whose fan beams together define a total angular range of only 180°. However, the examination zone contains a multitude of voxels who have been struck by radiation in all radiation source positions and it is advisable to take into account all available measuring values for these voxels in order to achieve an as attractive as possible signal-to-noise ratio. Therefore, hereinafter a difference will be made between voxels which have been irradiated from all radiation source positions and those which have not.

After the selection of a voxel in the examination zone whose absorption is to be reconstructed (step 109), in the step 110 it is first checked whether the relevant voxel has been irradiated from all radiation source positions.

Figure 6:
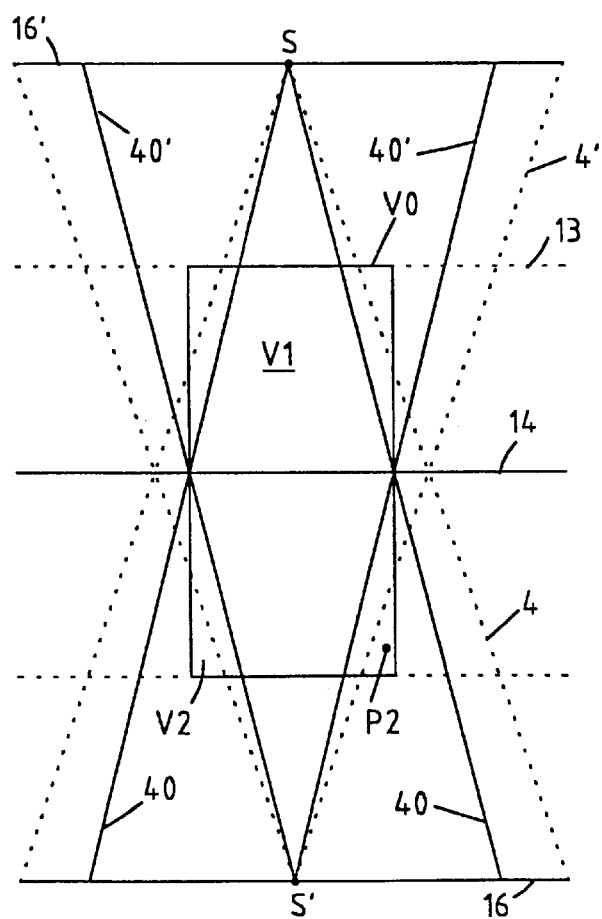
FIG. 6 shows the geometrical conditions in the examination zone.

To this end, reference is first made to FIG. 6 which shows the radiation source S which is denoted by a dot, the detector unit 16 which is symbolized by a line, and the radiation beam 4 in a first position relative to the axis of rotation 14. FIG. 6 also shows a second position of the radiation source S', 180° offset relative to the first position, the detector unit 16' and the radiation beam 4'. The examination zone 13 is also indicated in FIG. 6. The rays at the edges of the radiation beam 4, offset in the direction of the axis of rotation 14, are denoted by dashed lines. Solid lines, however, denote the rays 40 and 40' which bound the radiation beam after omission of the rays at the edge (step 107).

It can be demonstrated that all voxels within a flat, circular slab $V_0$ have been irradiated from an angular range of at least 180°. The side faces of this slice are defined by the points of intersection of the edge rays 40 and 40' with the axis of rotation 14. All voxels situated in the discus-shaped sub-volume VI defined by the edge rays 40 and 40' have then been irradiated from all radiation source positions, whereas the voxels situated in the sub-volume $V_2$, defined by the difference between $V_0$ and $V_1$, have "seen" the radiation source from an angle of at least 180° but less than 360° during the scanning motion.

If the test 110 reveals that the voxel selected in the step 109 is situated in the sub-volume $V_1$, i.e. that it has been irradiated from all radiation source positions, a backprojection during which each time that ray in each group is taken which extends through the relevant voxel is performed in the step 111. If no ray passes exactly through the center of the relevant voxel, the associated value must be determined by interpolation of the measuring values of neighboring rays.

If the test result in the step 110 is negative, a further test is performed in the step 112 so as to determine whether the selected voxel is situated in the sub-volume $V_2$ (i.e. if it has "seen" the radiation source at an angle of at least 180°); if this is not the case, the program proceeds to a further test 113 in which it is determined whether the absorption has already been reconstructed in all voxels of the FOV. If this is not the case, the steps 109 and further are executed again. In the case of a positive result, i.e. if the voxel selected in the step 109 is situated in the volume $V_2$, the groups to be taken into account for the reconstruction of the absorption in the voxel are selected in the step 118. In this respect reference is made to FIG. 7 which shows the circular scanning path 17 and the various radiation source positions thereon which are denoted by dots. The radiation source positions which are denoted by the references $S_{-2} \ldots S_0 \ldots S_2$ in FIG. 4 are characterized by the associated angles $\beta_{-2} \ldots \beta_0 \ldots \beta_2$ on the circle 17 in FIG. 7. As has already been described in conjunction with the steps 103 to 108, with each radiation source position there is associated a group of filtered measuring data produced by the rebinning operation.

Figure 7:
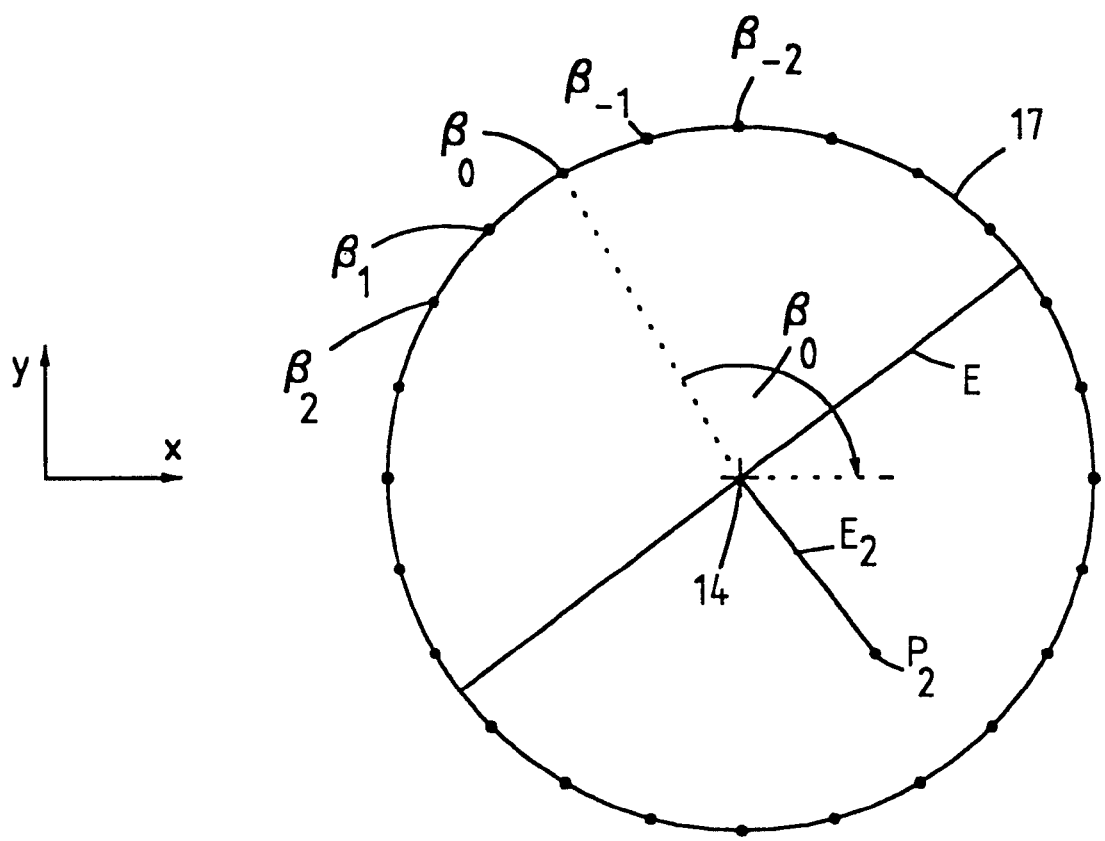
FIG. 7 shows a diagram for the selection of radiation source positions.

FIG. 7 also shows a voxel $P_2$ which, as indicated in FIG. 6, is situated in the sub-volume $V_2$. The reference $E_2$ denotes the plane which extends perpendicularly to the plane of drawing of FIG. 7 and is defined by the voxel $P_2$ and the axis of rotation 14. Finally, the reference E denotes a plane which intersects the plane $E_2$ in the axis of rotation.

It can be demonstrated that the voxel $P_2$ has been irradiated from all radiation source positions to the other side of the plane E. However, the voxel $P_2$ has received radiation from some, but not all, radiation source positions situated to this side of the plane E (in relation to the voxel).

Consequently, in the step 119 all groups of data produced by the rebinning and filtering are taken into account for the reconstruction, i.e. all groups which are associated with the radiation source positions (for example, $\beta_2 \ldots \beta_2$) situated to the other side of the plane E and together form an irradiation angle range of exactly 180. This irradiation angle range is necessary and suffices to reconstruct the absorption in the relevant voxel even when the backprojection performed by means of this data produces a signal-to-noise ratio which is inferior to that achieved by the backprojection performed in the step 111.

As soon as it is determined in the step 113 that all voxels in the selected FOV have been reconstructed, the execution of the method is terminated (step 114). The absorption values in the FOV can then be displayed (possibly in the form of slices) on a suitable display screen.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A computed tomography method comprising:
   generating, while using a radiation source, a conical radiation beam which traverses an examination zone or an object present therein,
   generating a circular relative motion, including a rotation about an axis of rotation, between the radiation source on the one side and the examination zone or the object on the other side, acquiring, while using a detector unit, measuring data which is dependent on the intensity in the radiation beam to the other side of the examination zone during the relative motion, and reconstructing the spatial distribution of the absorption within the examination zone from the acquired measuring data, wherein the step of reconstruction further comprises:

rebinning the measuring data so as to form a number of groups, each group containing a plurality of planes which extend parallel to one another and parallel to the axis of rotation and in each of which a respective fan beam is situated, one-dimensional filtering of the data produced by the rebinning in each group in a direction perpendicular to the direction of the planes, and reconstructing the spatial distribution of the absorption by backprojection of the filtered data of a plurality of groups.

2. A computed tomography method as claimed in claim 1, wherein the rebinning is performed on a respective flat and rectangular virtual detector which extends perpendicularly to the planes of each group and contains the axis of rotation.

3. A computed tomography method as claimed in claim 1, wherein the step of reconstructing further comprises reconstructing the absorption of voxels with an irradiation angle range of at least 180° while taking into account the filtered measuring data from exclusively the radiation source positions which are separated from the voxel by a plane which contains the axis of rotation and extends perpendicularly to the plane defined by the relevant voxel and the axis of rotation.

4. A computed tomography method as claimed in claim 1, wherein the step of reconstructing further comprises assigning voxels with an irradiation angle range of 360° to a first sub-volume, assigning voxels with an irradiation angle range of at least 180° but less than 360° to a second sub-volume, reconstructing the absorption of the voxels in the first sub-volume while taking into account measuring data from all radiation source positions, and reconstructing the absorption of the voxels in the second sub-volume while taking into account the filtered measuring data from exactly so many radiation source positions that an irradiation angle range of 180° is obtained.

5. A computed tomography apparatus comprising:

a radiation source a detector unit which is coupled thereto, a drive device for making an object present in the examination zone and the detector device perform a rotation about the axis of rotation relative to one another, and a reconstruction unit for reconstructing the spatial distribution of the absorption within the examination zone from the measuring data acquired by the detector unit, wherein the reconstruction unit further comprises means for the rebinning of the measuring data so as to form a plurality of groups, each group containing several planes which are parallel to the axis of rotation and each of which contains a fan beam, means for the one-dimensional filtering of the data, produced by the rebinning, of each group in the direction perpendicular to the direction of the planes, and means for the reconstruction of the spatial distribution of the absorption from the filtered data of different groups.

6. A computed tomography apparatus, as claimed in claim 5, further comprising a collimator device having edges which are mutually offset in the direction of the axis of rotation and which are shaped in such a manner that the conical radiation beam has an aperture at its center which is smaller than that at its edges.

* * * * *